(12) United States Patent
Balko et al.

(10) Patent No.: US 9,320,863 B2
(45) Date of Patent: Apr. 26, 2016

(54) SYSTEM AND METHOD FOR INEXSUFFLATING A SUBJECT

(75) Inventors: Norbert Hans Balko, Eindhoven (NL);
Seung Hyun Lee, Eindhoven (NL);
Peter Douglas Hill, Eindhoven (NL);
Christopher Wayne McDaniel,
Eindhoven (NL)

(73) Assignee: KONINKLIJKE PHILIPS N.V.,
Eindhoven (NL)

( * ) Notice: Subject to any disclaimer, the term of this patent is extended or adjusted under 35 U.S.C. 154(b) by 167 days.

(21) Appl. No.: 13/994,324

(22) PCT Filed: Dec. 16, 2011

(86) PCT No.: PCT/IB2011/055726
§ 371 (c)(1),
(2), (4) Date: Jun. 14, 2013

(87) PCT Pub. No.: WO2012/085787
PCT Pub. Date: Jun. 28, 2012

(65) Prior Publication Data
US 2013/0269698 A1   Oct. 17, 2013

Related U.S. Application Data

(60) Provisional application No. 61/425,392, filed on Dec. 21, 2010.

(51) Int. Cl.
| A61M 11/00 | (2006.01) |
| A61M 16/00 | (2006.01) |
| A61M 16/04 | (2006.01) |
| A61M 16/06 | (2006.01) |
| A61M 16/08 | (2006.01) |

(52) U.S. Cl.
CPC ....... *A61M 16/0057* (2013.01); *A61M 16/0006* (2014.02); *A61M 16/0009* (2014.02);
(Continued)

(58) Field of Classification Search
CPC .................. A61M 16/0051; A61M 2230/005;
A61M 16/0069; A61M 2016/0021; A61M 16/00; A61M 2016/0036; A61M 16/0057; A61M 2016/0042; A61M 2205/502; A61M 16/0465; A61M 16/0666; A61M 16/0875; A61M 16/0006; A61M 16/0009
USPC ........................... 128/204.18, 204.21, 204.23
See application file for complete search history.

(56) References Cited

U.S. PATENT DOCUMENTS

| 2003/0106554 | A1* | 6/2003 | de Silva et al. .......... 128/204.22 |
| 2007/0199566 | A1  | 8/2007 | Be'eri |

(Continued)

FOREIGN PATENT DOCUMENTS

| CN | 1849150 A    | 10/2006 |
| CN | 101505820 A  | 8/2009  |
| CN | 101553268 A  | 10/2009 |

(Continued)

*Primary Examiner* — Steven Douglas
(74) *Attorney, Agent, or Firm* — Michael W. Haas (57) ABSTRACT

A system for controlling machine-induced expiratory airflow of a subject, the subject having an airway, the system comprising: a pressure generator (140) configured to generate a pressurized flow of breathable gas for delivery to the airway of the subject; and one or more processors (110) configured to execute computer program modules, the computer program modules comprising: a control module (170) configured to control the pressure generator a metric determination module (154) configured to determine a value of a flow metric during expiration by the subject, a flow analysis module (156) configured to compare the determined value of the flow metric with a target level of the flow metric; and an adjustment module (160) configured to adjust one or more of exsufflation pressure.

15 Claims, 5 Drawing Sheets

(52) U.S. Cl.
 CPC ....... *A61M16/0051* (2013.01); *A61M 16/0465* (2013.01); *A61M 16/0666* (2013.01); *A61M 16/0875* (2013.01); *A61M 2016/0042* (2013.01); *A61M 2205/502* (2013.01)

(56) References Cited

U.S. PATENT DOCUMENTS

2009/0293877 A1* 12/2009 Blanch et al. ............ 128/204.23
2009/0301486 A1* 12/2009 Masic ....................... 128/204.21
2010/0051029 A1*  3/2010 Jafari et al. .............. 128/204.23
2010/0101583 A1   4/2010 Chen
2012/0247471 A1* 10/2012 Masic et al. ............. 128/204.23

FOREIGN PATENT DOCUMENTS

| JP | 2009509610 A | 3/2012 |
| WO | WO2007054829 A2 | 5/2007 |
| WO | WO2010058308 A2 | 5/2010 |

\* cited by examiner

SYSTEM AND METHOD FOR INEXSUFFLATING A SUBJECT

CROSS-REFERENCE TO RELATED APPLICATIONS

This patent application claims the priority benefit under 35 U.S.C. §371 of international patent application no. PCT/IB2011/055726, filed Dec. 16, 2011, which claims the priority benefit under 35 U.S.C. §119(e) of U.S. Provisional Application No. 61/425,392 filed on Dec. 21, 2010, the contents of which are herein incorporated by reference.

BACKGROUND OF THE INVENTION

1. Field of the Disclosure

The invention relates to inexsufflation of a subject during which peak expiratory flow rate is controlled.

2. Description of the Related Art

Coughing, also known as "airway clearance", is a normal function of everyday life for most people. Inhaled air is drawn in slowly (<1 LPS). Then, the glottis closes and the expiratory muscles contract, increasing the subglottic pressure. To begin the cough, the glottis opens and the initial flow is the decompression of the air in the trachea. The lungs continue to empty at a rate of roughly 4 LPS until the lungs are sufficiently decompressed.

Some people, due to injury, disease, or even thoracic surgery, find it difficult to impossible to cough effectively on their own. For these people, assisted or artificial airway clearance is prescribed.

Artificial airway clearance can be achieved via many methods. One such method employs the use of a mechanical in-exsufflator (MI-E). A MI-E is a medical device that delivers positive airway pressure through the mouth, nose, or a tracheostomy gently filling the lungs to capacity (insufflation). It then very abruptly reverses pressure which generates an explosive expiratory flow, mimicking a cough (exsufflation).

In conventional systems, determining the initial (optimal) settings for a particular patient can be imprecise and/or inaccurate. Each patient has respiratory characteristics unique to them (e.g. airway resistance, lung compliance, patient effort, etc.), which can change over the course of the condition with which they are afflicted. Usually, through trial and error, and while relying on past experience, a physician arrives at settings that may or may not be optimal. Conventional systems may not provide confirmation that acceptable settings have been reached.

SUMMARY OF THE INVENTION

Accordingly, it is an object of the present invention to provide an exsufflation method that overcomes the shortcomings of a conventional exsufflation methods. This object is achieved according to one embodiment of the present invention by providing a method for controlling machine-induced expiratory airflow of a subject, the subject having an airway. In one embodiment, the method comprises generating a pressurized flow of breathable gas for delivery to the airway of a subject at an insufflation pressure level prior to a transition time; identifying the transition time based on one or more insufflation parameters; responsive to identification of the transition time, reducing pressure of the pressurized flow of breathable gas to an exsufflation pressure level during an inexsufflation transition; determining a value of a flow metric during expiration by the subject, wherein the value of the flow metric indicates an amount of gas flow out of the lungs of the subject during exsufflation; comparing the determined value of the flow metric with a target level of the flow metric that corresponds to a target flow rate of gas out of the lungs of the subject; adjusting one or more of exsufflation pressure, one or more insufflation parameters, or one or more parameters of the inexsufflation transition based on the comparison of the determined value of the flow metric with the target level of the flow metric; and implementing the adjusted exsufflation pressure, the adjusted one or more insufflation parameters, and/or the adjusted one or more parameters of the inexsufflation transition during a subsequent breath.

Another aspect of the disclosure relates to a system for controlling machine-induced expiratory airflow of a subject, the subject having an airway. In one embodiment, the system comprises a pressure generator and one or more processors. The pressure generator is configured to generate a pressurized flow of breathable gas for delivery to the airway of the subject. The one or more processors are configured to execute computer program modules including a control module, a metric determination module, a flow analysis module, and an adjustment module. The control module is configured to control the pressure generator such that the pressure of the pressurized flow of breathable gas at the airway of the subject prior to a transition time is at an insufflation pressure level, and such that responsive to the transition time the pressure level of the pressurized flow of breathable gas at the airway of the subject is reduced to an exsufflation pressure level during an inexsufflation transition, the control module being configured to identify the transition time based on one or more insufflation parameters. The metric determination module is configured to determine a value of a flow metric during expiration by the subject, wherein the flow metric indicates flow out of the lungs of the subject during exsufflation. The flow analysis module is configured to compare the determined value of the flow metric with a target level of the flow metric. The adjustment module is configured to adjust one or more of exsufflation pressure, one or more insufflation parameters, or one or more parameters of the inexsufflation transition based on comparison of the determined value of the flow metric with the target level of the flow metric by the flow analysis module.

Yet another aspect of the disclosure relates to a system configured to control machine-induced expiratory airflow of a subject, the subject having an airway. In one embodiment, the system comprises means for generating a pressurized flow of breathable gas for delivery to the airway of a subject at an insufflation pressure level prior to a transition time; means for identifying the transition time based on one or more insufflation parameters; means for, responsive to identification of the transition time, reducing pressure of the pressurized flow of breathable gas to an exsufflation pressure level during an inexsufflation transition pressure of the pressurized flow of breathable gas to a second pressure level subsequent to the transition time to initiate expiration by the subject; means for determining value of a flow metric during expiration by the subject, wherein the flow metric indicates gas flow out of the lungs of the subject during exsufflation; means for comparing the determined value of the flow metric with a target level of the flow metric; means for adjusting one or more of exsufflation pressure, one or more insufflation parameters, or one or more parameters of the inexsufflation transition based on the comparison of the determined value of the flow metric with the target level of the flow metric; and means for implementing the adjusted exsufflation pressure, the adjusted one or more insufflation parameters, and/or the adjusted one or more parameters of the inexsufflation transition during a subsequent breath.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment, the structural components illustrated herein are drawn to scale. It is to be expressly understood, however, that the drawings are for the purpose of illustration and description only and are not a limitation. In addition, it should be appreciated that structural features shown or described in any one embodiment herein can be used in other embodiments as well. It is to be expressly understood, however, that the drawings are for the purpose of illustration and description only and are not intended as a definition of limits.

DETAILED DESCRIPTION OF THE EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
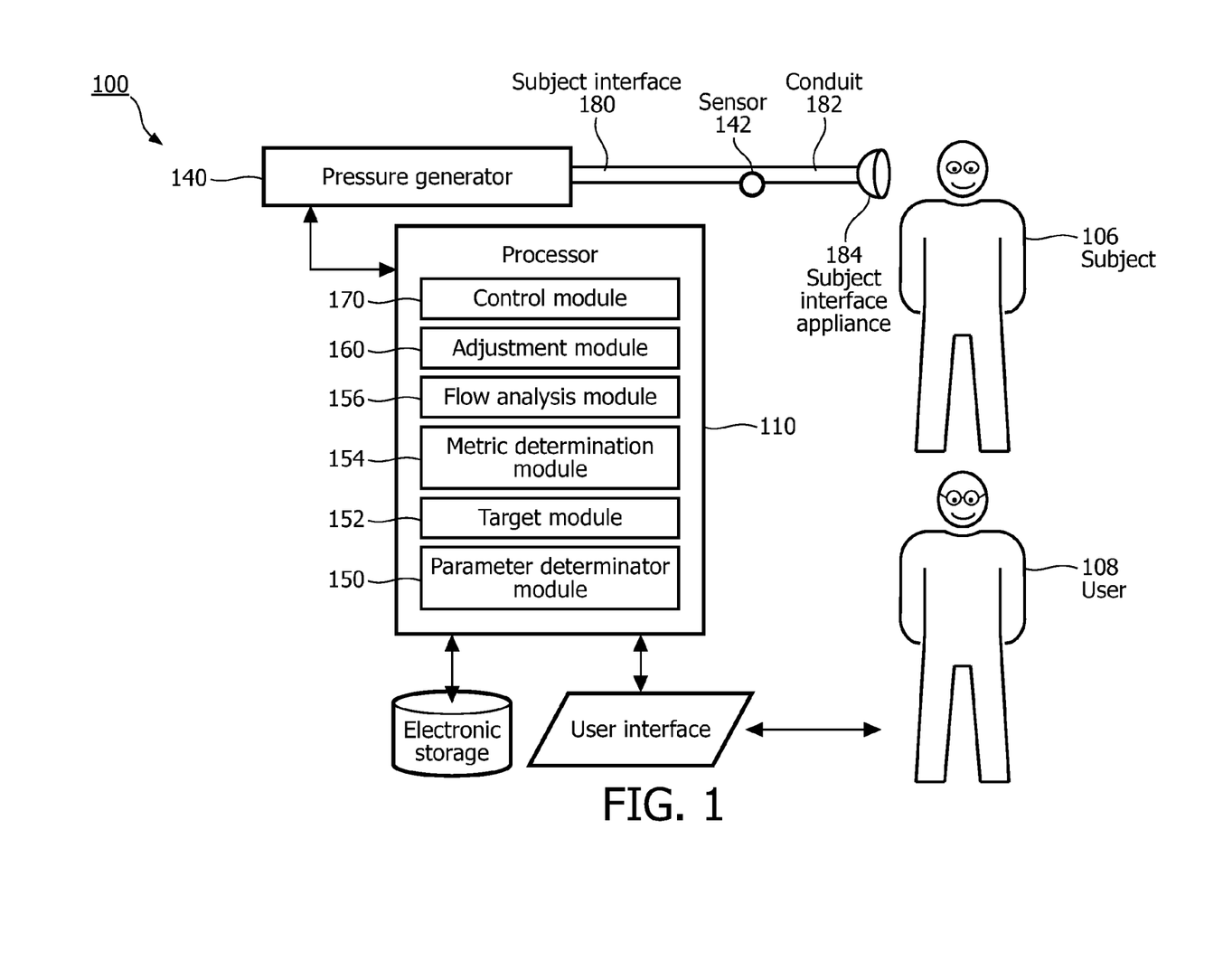
FIG. 1 illustrates a system configured to insufflate and exsufflate a subject.

FIG. 1 illustrates a system 100 configured to insufflate and exsufflate (hereafter "inexsufflate") a subject 106. In particular, system 100 inexsufflates subject 106 such that peak flow during exsufflation, or expiration, is monitored, and is controlled by adjusting one or more insufflation parameters and/or parameters of transitions between insufflation and exsufflation. This may provide for more precise, customized therapy for subject 106 than is provided by conventional inexsufflation systems in which expiratory flow may not be monitored. In one embodiment, system 100 comprises a processor 110, a user interface 120, an electronic storage 130, a pressure generator 140, one or more sensors 142, and/or other components.

Pressure generator 140 is configured to provide a pressurized flow of breathable gas for delivery to the airway of the subject. The pressure generator 140 is configured such that one or more gas parameters of the pressurized flow of breathable gas are controlled in accordance with a therapy regimen to inexsufflate subject 106. The one or more gas parameters may include, for example, one or more of flow, pressure, humidity, velocity, acceleration, and/or other parameters. In one embodiment, pressure generator 140 is a device dedicated to mechanical inexsufflation. In one embodiment, pressure generator 140 is a ventilator or positive airway pressure device configured to provide types of therapy other than inexsufflation.

The pressurized flow of breathable gas is delivered from the pressure generator 140 to the airway of subject 106 by a subject interface 180. The subject interface 180 may include a conduit 182 and/or a subject interface appliance 184.

Conduit 182 may be a flexible length of hose, or other conduit, that places subject interface appliance 184 in fluid communication with pressure generator 140. The conduit 182 forms a flow path through which the pressurized flow of breathable gas is communicated between subject interface appliance 184 and pressure generator 140.

Subject interface appliance 184 is configured to deliver the pressurized flow of breathable gas to the airway of subject 106. As such, the subject interface appliance may include any appliance suitable for this function. In one embodiment, pressure generator 140 is a dedicated inexsufflation device and subject interface appliance 184 is configured to be removably coupled with another interface appliance being used to deliver respiratory therapy to subject 106. For example, the subject interface appliance may be configured to engage with and/or be inserted into an endotracheal tube, a tracheotomy portal, and/or other interface appliances. In one embodiment, subject interface appliance 184 is configured to engage the airway of subject 106 without an intervening appliance. In this embodiment, subject interface appliance 184 may include one or more of an endotracheal tube, a nasal cannula, a tracheotomy tube, a nasal mask, a nasal/oral mask, a full face mask, a total face mask, a partial rebreathing mask, or other interface appliances that communicate a flow of gas with an airway of a subject.

In one embodiment, electronic storage 130 comprises electronic storage media that electronically stores information. The electronic storage media of electronic storage 130 may include one or both of system storage that is provided integrally (i.e., substantially non-removable) with system 100 and/or removable storage that is removably connectable to system 100 via, for example, a port (e.g., a USB port, a firewire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 100 to function properly. Electronic storage 130 may be a separate component within system 100, or electronic storage 130 may be provided integrally with one or more other components of system 100 (e.g., processor 110).

User interface 120 is configured to provide an interface between system 100 and a user (e.g., user 108, subject 106, a caregiver, a therapy decision-maker, etc.) through which the user may provide information to and receive information from system 100. This enables data, results, and/or instructions and any other communicable items, collectively referred to as "information," to be communicated between the user and system 100. Examples of interface devices suitable for inclusion in user interface 120 include a keypad, buttons, switches, a keyboard, knobs, levers, a display screen, a touch screen, speakers, a microphone, an indicator light, an audible alarm, and a printer.

It is to be understood that other communication techniques, either hard-wired or wireless, are also contemplated by the present invention as user interface 120. For example, in one embodiment, user interface 120 may be integrated with a removable storage interface provided by electronic storage 130. In this example, information may be loaded into system 100 from removable storage (e.g., a smart card, a flash drive, a removable disk, etc.) that enables the user(s) to customize the implementation of system 100. Other exemplary input devices and techniques adapted for use with system 100 as user interface 120 include, but are not limited to, an RS-232 port, RF link, an IR link, modem (telephone, cable or other). In short, any technique for communicating information with system 100 is contemplated as user interface 120.

Sensor 142 is configured to generate output signals conveying information related to one or more gas parameters of the pressurized flow of breathable gas. The one or more parameters may include, for example, one or more of a flow, a volume, a pressure, a composition (e.g., concentration(s) of one or more constituents), humidity, temperature, acceleration, velocity, acoustics, changes in a parameter indicative of respiration, and/or other fluid parameters. In one embodiment, sensor 142 includes a flow sensor and/or a pressure sensor. Sensor 142 may include one or more sensors that measure such parameters directly (e.g., through fluid communication with the pressurized flow of breathable gas at pressure generator 140 or in subject interface 180). Sensor 142 may include one or more sensors that generate output signals related to one or more fluid parameters of the pressurized flow of breathable gas indirectly. For example, sensor 142 may generate an output based on an operating parameter of pressure generator 140 (e.g., a valve driver or motor current, voltage, rotational velocity, and/or other operating parameters), and/or other sensors.

The illustration of sensor 142 as including a single member in FIG. 1 is not intended to be limiting. In one embodiment sensor 142 includes a plurality of sensors generating output signals as described above. Similarly, the position of sensor 142 in FIG. 1 is not intended to be limiting. Sensor 142 may include one or more sensors located within pressure generator 140 and/or subject interface 180. The output signals generated by sensor 142 may be transmitted to processor 110, user interface 120, and/or electronic storage 130. This transmission may be accomplished via wired and/or wirelessly.

Processor 110 is configured to provide information processing capabilities in system 100. As such, processor 110 may include one or more of a digital processor, an analog processor, a digital circuit designed to process information, an analog circuit designed to process information, a state machine, and/or other mechanisms for electronically processing information. Although processor 110 is shown in FIG. 1 as a single entity, this is for illustrative purposes only. In some implementations, processor 110 may include a plurality of processing units. These processing units may be physically located within the same device, or processor 110 may represent processing functionality of a plurality of devices operating in coordination.

As is shown in FIG. 1, processor 110 may be configured to execute one or more computer program modules. The one or more computer program modules may include one or more of a parameter determination module 150, a target module 152, a metric determination module 154, a flow analysis module 156, an adjustment module 160, a control module 170, and/or other modules. Processor 110 may be configured to execute modules 150, 152, 154, 156, 160, and/or 170 by software; hardware; firmware; some combination of software, hardware, and/or firmware; and/or other mechanisms for configuring processing capabilities on processor 110.

It should be appreciated that although modules 150, 152, 154, 156, 160, and 170 are illustrated in FIG. 1 as being co-located within a single processing unit, in implementations in which processor 110 includes multiple processing units, one or more of modules 150, 152, 154, 156, 160, and/or 170 may be located remotely from the other modules. The description of the functionality provided by the different modules 150, 152, 154, 156, 160, and/or 170 described below is for illustrative purposes, and is not intended to be limiting, as any of modules 150, 152, 154, 156, 160, and/or 170 may provide more or less functionality than is described. For example, one or more of modules 150, 152, 154, 156, 160, and/or 170 may be eliminated, and some or all of its functionality may be provided by other ones of modules 150, 152, 154, 156, 160, and/or 170. As another example, processor 110 may be configured to execute one or more additional modules that may perform some or all of the functionality attributed below to one of modules 150, 152, 154, 156, 160, and/or 170.

Control module 170 is configured to control pressure generator 140 to adjust the parameters of the pressurized flow of breathable gas in accordance with the therapy regimen. In one embodiment, the therapy regimen dictates that control module 170 control pressure generator 140 such that the pressurized flow of breathable gas is delivered to the airway of subject 106 at a first pressure level during insufflation. The first pressure level is sufficiently high that the lungs of subject 106 are at least partially filled during insufflation, or inspiration. At a transition time, control module 170 controls pressure generator 140 to reduce the pressure of the pressurized flow of breathable gas with sufficient abruptness that expiratory flow through the airway of subject 106 is sufficient to remove sputum and/or other debris from the airway and/or lungs of subject 106. The pressure may be reduced at the transition time from the first pressure level to a second pressure level that is substantially lower than the first pressure level. The second pressure level may, for example, be a negative pressure. After expiration is complete, control module 170 then controls pressure generator 140 to return the pressure of the pressurized flow of breathable gas to the first pressure level to facilitate another inspiration in preparation for another transition time and subsequent expiration to remove additional sputum and/or other debris. After a series of these inexsufflations, inexsufflation may be ceased.

Control module 170 is configured to determine the transition time based on one or more insufflation parameters. The insufflation parameters may include one or more of an insufflation pressure, an insufflation volume, an insufflation flow, an insufflation time period, and/or other parameters of insufflation. An insufflation time may include an amount of time since the commencement of insufflation, an amount of time since another insufflation parameter has reached or breached a threshold level (e.g., time with flow above a flow level, time with pressure above a pressure level, etc.). The determination of the transition time may be threshold based. For example, responsive to one or more of the insufflation parameters breathing a threshold level (e.g., insufflation pressure, insufflation volume, insufflation time, etc.), the control module may determine that the transition time has arrived. The threshold may be determined to correspond to the point in time at which sufficient gas has been received into the lungs of subject 106 for a productive exsufflation to commence.

The parameter determination module 150 is configured to determine one or more gas parameters of the pressurized flow of breathable gas during inexsufflation by system 100. The one or more gas parameters may include one or more of pressure, flow, volume, composition, and/or other parameters. The parameter determination module 150 may determine the parameters based on output signals generated by sensor 142. The parameters of the pressurized flow of breathable gas may be determined for gas at pressure generator 140, at or near the airway of subject 106, and/or at other locations along the path between pressure generator 140 and subject 106. In one embodiment, the parameters of the pressurized flow of breathable gas determined by parameter determination module 150 are implemented by control module 170 in a feedback manner as control module 170 controls pressure generator 140 to provide the pressurized flow of breathable gas at specific levels for the parameters (e.g., at specific pressure, flow, and/or volume levels).

Target module 152 is configured to obtain a target level of a flow metric. The target level is the level of the flow metric that corresponds to the flow at which gas should be drawn out of the lungs of subject 106 during expiration. The target module may obtain the target level from a user via user interface 120. This may include receiving an input of a specific target level, an input of a user name or identification that has been previously associated with a specific target level, and/or other input from which a target level can be obtained and/or determined.

The flow metric is a metric that is indicative of flow during exsufflation. This may simply include flow. However, during mechanical inexsufflation, at the beginning of expiration there is a spike in expiratory flow that does not represent productive gas flow. Instead, this spike corresponds to an initial flow of gas from the upper airway of subject 106 that is not productive in removing sputum and/or other debris from the airway of subject 106. As such, a metric other than simple peak flow may be used to quantify exsufflation flow for the purposes of system 100.

Figure 3:
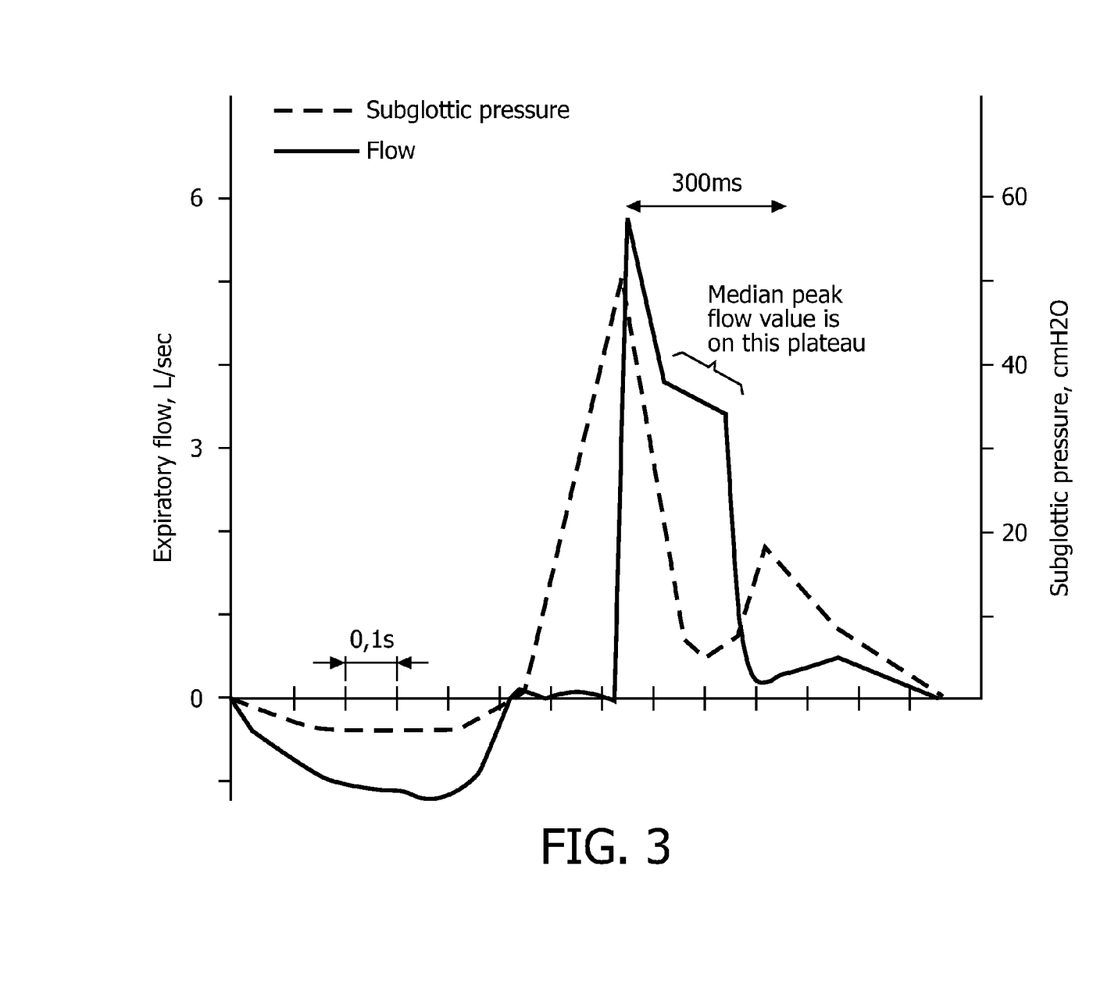
FIG. 3 illustrates plots of airway pressure and flow during insufflation and exsufflation.

By way of illustration, FIG. 3 shows plots of both flow and pressure at or near the airway of a subject undergoing inexsufflation with respect to time. As can be seen in FIG. 3, at a transition time pressure is reduced from a relatively high first pressure level to a relatively low second pressure level. This corresponds to the transition time described above at which expiration is initiated with sufficient flow to remove sputum and/or other debris from the airway of the subject. At the transition time, the expiratory flow spikes as the gas in the upper airway rushes out of the subject. Just after this initial spike, an initial plateau in flow can be observed. This initial plateau typically occurs within 300 ms of the transition time, as is illustrated in FIG. 3.

An example of a flow metric indicative of productive exsufflation flow is the level of the initial flow plateau illustrated in FIG. 3 (e.g., the median or mean value of the plateau). Other examples include, without limitation, an amount of time that a flow threshold is breached (e.g., time over 150 LPM of flow), a calculated or estimated time derivative of flow during exsufflation, an amount of time a threshold of a calculated or estimated time derivative of flow is breached during exsufflation, an amount of time from the transition time until a calculated or estimated second time derivative of flow remains negative, and/or other metrics determined from flow during exsufflation. Pressure-based examples of a flow metric (e.g., indicating flow during exsufflation) include an amount of time from the transition time until pressure decays to a threshold level (the threshold level may be an amount or a percentage of pressure at the transition time), and/or other pressure-based metrics that indicate flow during exsufflation. Volume-based examples of a flow metric include an amount of time from the transition time until the volume of exsufflated gas reaches a threshold level (the threshold level may be an amount or a percentage of the inhaled tidal volume), and/or other volume-based metrics that indicate flow during exsufflation.

Returning to FIG. 1, metric determination module 154 is configured to determine a value of the flow metric during expiration. The metric determination module is configured to make this determination based on output signals generated by sensor 142 and/or based on the gas parameters determined by parameter determination module 150.

Flow analysis module 156 is configured to compare the values of the flow metric for expirations (as determined by metric determination module 154) with the target level of the flow metric (as obtained by target module 152). For a given expiration, this comparison may include determining a difference between the determined value of the flow metric and the target level of the flow metric. The difference may be determined as a difference amount, a percent difference, and/or other differences.

Adjustment module 160 is configured to determine an adjustment to one or more of exsufflation pressure, the insufflation parameters used by control module 170 to determine transition times, the inexsufflation transition from the first pressure level to the second pressure level, and/or other parameters. The exsufflation pressure, the insufflation parameters and/or the inexsufflation transition are adjusted such that for a subsequent inexsufflation, the flow metric during exsufflation will be closer to the target level of the flow metric.

For example, if the comparison of the value of the flow metric with the target level of the flow metric indicates that the expiratory flow rate is less than the flow rate corresponding to the target level of the flow metric, the adjustment module 160 adjusts the exsufflation pressure lower (e.g., with a larger negative magnitude) to increase the flow out of the lungs of subject 106. The insufflation parameters may be adjusted to increase the amount of gas in the lungs of subject 106 during exsufflation. The inexsufflation transition may be adjusted to increase flow out of the lungs of subject 106 during exsufflation. Increasing the amount of gas in the lungs of subject 106 may include increasing one or more of an insufflation pressure, an insufflation volume, an insufflation flow, and/or an insufflation time period. Adjusting the inexsufflation transition to increase flow out of the lungs of subject 106 may include reducing the exsufflation pressure (e.g., increases the magnitude of a negative pressure), reducing the amount of time it takes to transition from the insufflation pressure to the exsufflation pressure, and/or increasing the rate of change in the pressure of the pressurized flow of breathable gas from the insufflation pressure to the exsufflation pressure so that the expiratory flow rate will be increased in subsequent inexsufflations.

Figure 4:
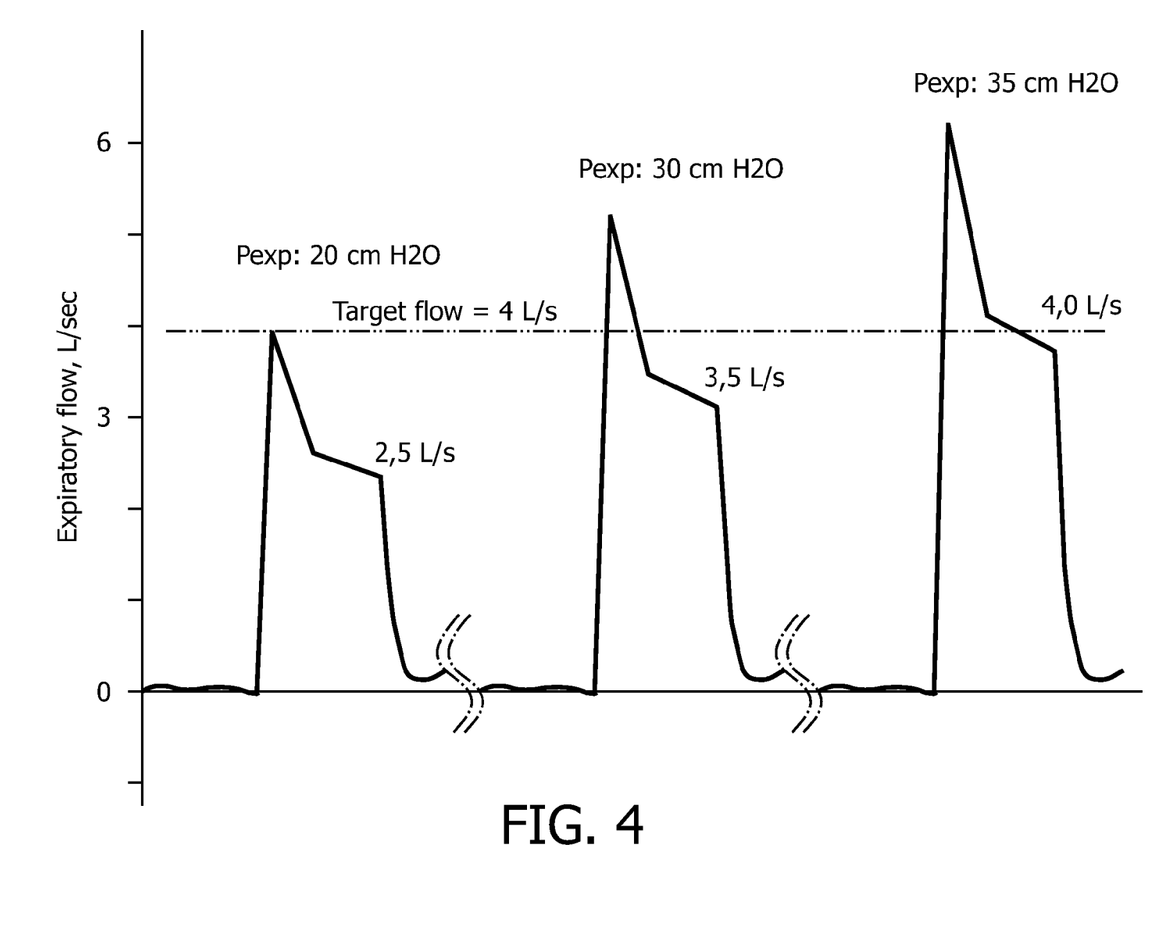
FIG. 4 illustrates a plot of airway flow during a series of insufflations and exsufflations.

By way of illustration, FIG. 4 shows a plot of flow during inexsufflation versus time as the exsufflation pressure level is adjusted. Specifically, the plot of FIG. 4 illustrates three peaks in expiratory flow corresponding to three transition times. FIG. 4 further indicates that the magnitude of the exsufflation pressure level is increased for the peaks from left to right. This means that the pressure in the airway of the subject is lower (e.g., with greater negative magnitude) for peaks to the right. As the exsufflation pressure level is lowered, the exsufflation flow rate of the peaks are increased towards an illustrated target flow rate.

Returning to FIG. 1, the magnitude of the adjustments determined and applied by adjustment module 160 to exsufflation pressure, one or more insufflation parameters, the inexsufflation transition, and/or or other parameters may be derived in any number of ways. For example, the magnitude of adjustments may be a predetermined incremental amount. As another example, the magnitude may be determined based on a difference between the determined value of the flow metric and the target level of the flow metric. This would result in larger adjustments to the exsufflation pressure, the insufflation parameters, and/or the inexsufflation transition in instances where the determined value of the flow metric and the target level of the flow metric are relatively far apart, and smaller adjustments in instances where the determined value of the flow metric is relatively close to the target level of the flow metric. As yet another example, the magnitude of adjustments may be impacted by user input (e.g., received through user interface 120). For instance, a user may set the magnitude of adjustments, set limits for the magnitude of adjustments, and/or provide other input used to determine adjustments to the exsufflation pressure, the insufflation parameters, and/or the inexsufflation transition by adjustment module 160.

At the outset of therapy by system 100 (or at sometime thereafter), a user may set one or more therapy parameters used to govern the functionality described herein. These therapy parameters may include one or more of a parameter impacting the magnitude of adjustments to the exsufflation pressure, the insufflation parameters, and/or the inexsufflation transition; a maximum for exsufflation pressure, an insufflation parameter, and/or a parameter of the inexsufflation transition; a minimum for exsufflation pressure, an insufflation parameter, and/or a parameter of the inexsufflation transition; an initial level for exsufflation pressure, an insufflation parameter, and/or a parameter of the inexsufflation transition; the target level of the flow metric (e.g., as described above), and/or other therapy parameters. Selection and/or input of one or more of these parameters may be received by system 100 via user interface 120. Maximum and/or minimum levels for exsufflation pressure, an insufflation parameter, and/or a parameter of the inexsufflation transition may be implemented by adjustment module 160 as limits that constrain adjustment of the exsufflation pressure, the insufflation parameters, and/or the parameters of the inexsufflation transition. These limits may be set to maintain the comfort of subject 106, the effectiveness of the therapy, and/or based on other considerations.

Figure 2:
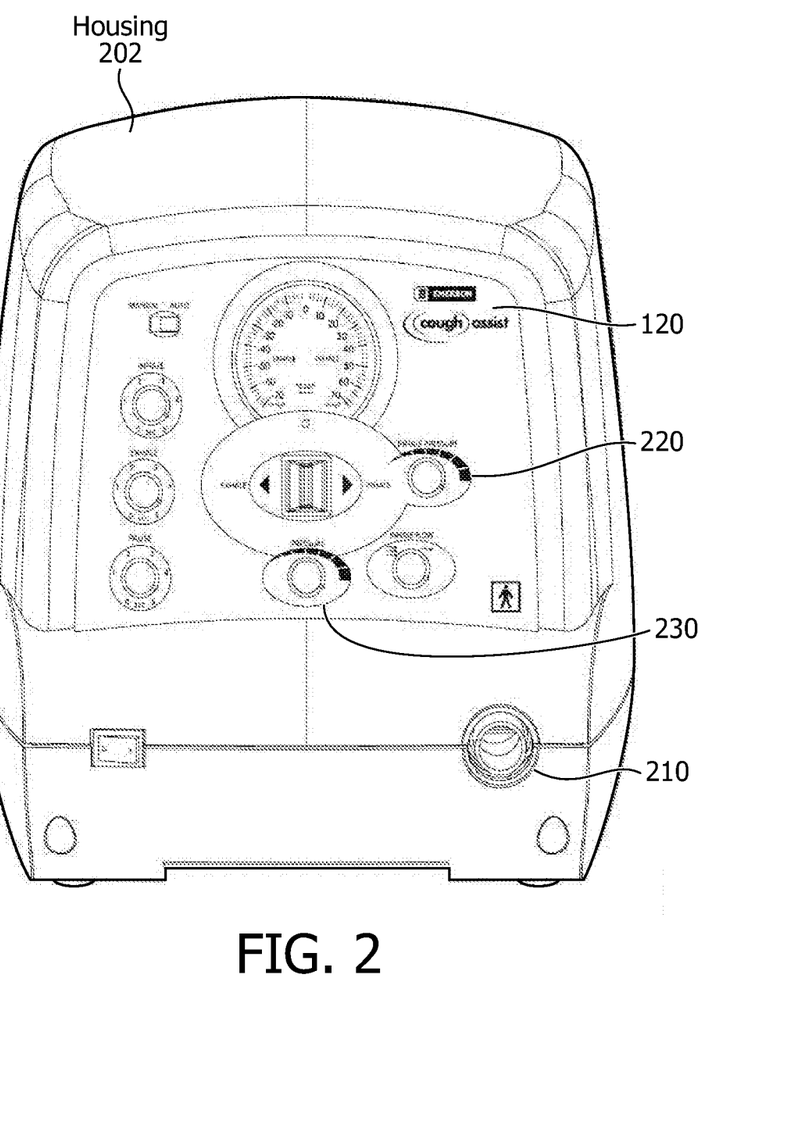
FIG. 2 illustrates a system configured to insufflate and exsufflate a subject.

FIG. 2 illustrates one embodiment of system 100 in which some of the components are housed in a housing 202. A port 210 is formed in housing 202. The port is configured to interface with the subject interface to communicate the pressurized flow of breathable gas therewith. In the embodiment shown in FIG. 2, user interface 120 is carried on housing 202. The user interface 120 is shown as including inhale pressure knob 220 and (exhale) pressure knob 230, which are used to set a first pressure level and a second pressure level for the inexsufflation.

Figure 5:
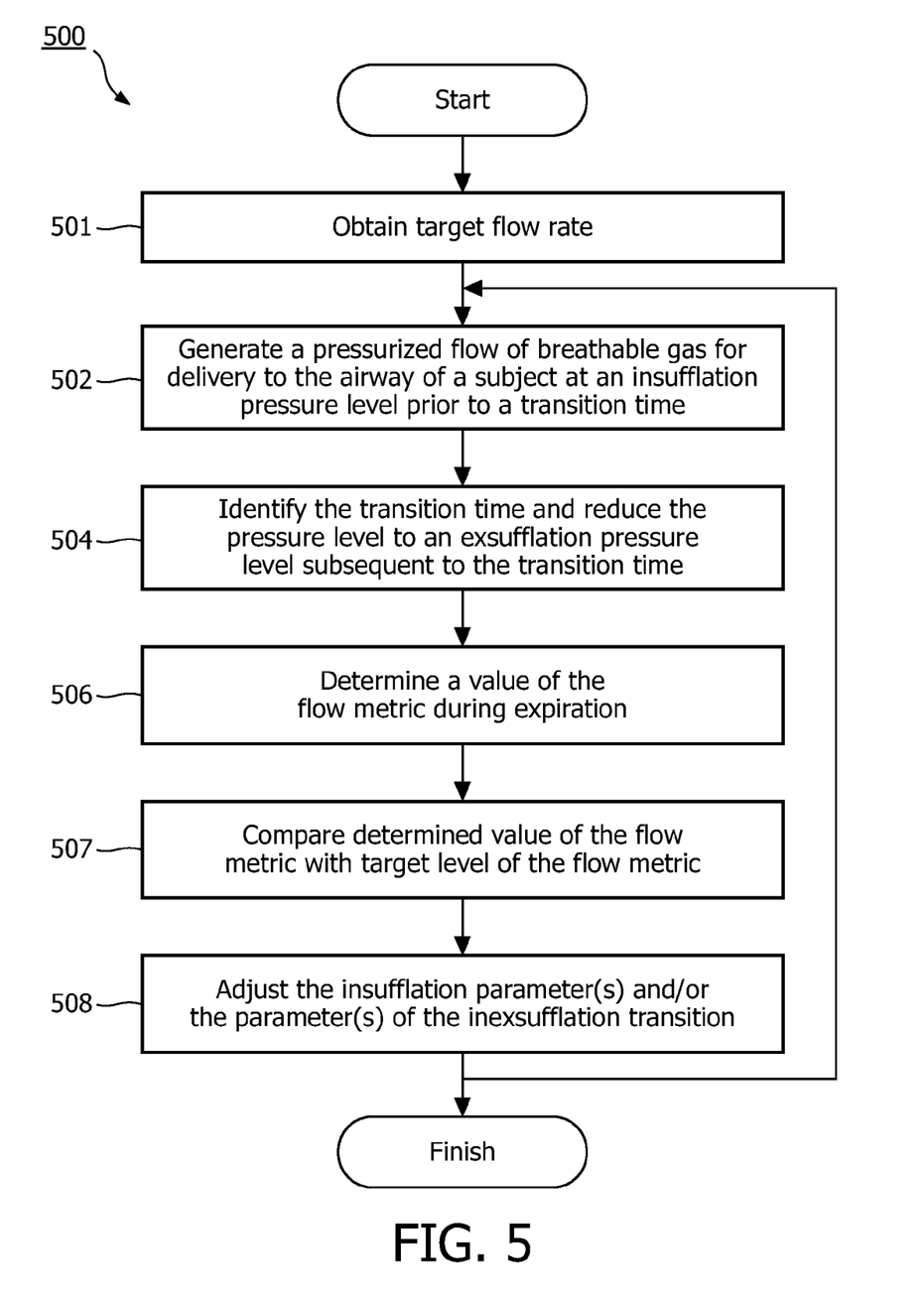
FIG. 5 illustrates a method of insufflating and exsufflating a subject.

FIG. 5 illustrates a method 500 of inexsufflating a subject. The operations of method 500 presented below are intended to be illustrative. In some embodiments, method 500 may be accomplished with one or more additional operations not described, and/or without one or more of the operations discussed. Additionally, the order in which the operations of method 500 are illustrated in FIG. 5 and described below is not intended to be limiting.

In some embodiments, method 500 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 500 in response to instructions stored electronically on an electronic storage medium. The one or more processing devices may include one or more devices configured through hardware, firmware, and/or software to be specifically designed for execution of one or more of the operations of method 500.

At an operation 501, a target level of a flow metric is obtained. The target level of the flow metric corresponds to the expiratory flow rate that should be attained to exsufflate the subject. The target level of the flow metric may be obtained from user input and/or from other sources or determinations. In one embodiment, operation 501 is performed by a target module similar to or the same as target module 152 (shown in FIG. 1 and described above).

At an operation 502, a pressurized flow of breathable gas is generated for delivery to the airway of the subject. The pressurized flow of breathable gas is generated at an insufflation pressure level prior to a transition time. The insufflation pressure level is sufficiently high to inflate the lungs of the subject during inspiration prior to the transition time. In one embodiment, operation 502 is performed by a pressure generator similar to or the same as pressure generator 140 (shown in FIG. 1 and described above) under control of a control module similar to or the same as control module 170 (shown in FIG. 1 and described above).

At an operation 504, responsive to occurrence of the transition time, the pressure of the pressurized flow of breathable gas is reduced to an exsufflation pressure level during an inexsufflation transition. The transition time may be detected based one or more insufflation parameters. The one or more insufflation parameters may include one or more of an insufflation pressure, an insufflation volume, an insufflation flow, an insufflation time period, and/or other parameters. The exsufflation pressure level is sufficiently low to draw gas out of the lungs of the subject to facilitate expiration by the subject. The expiration may be characterized by an expiratory flow through the airway of the subject that is sufficient to exsufflate the subject. The exsufflation pressure level may be a negative pressure. The inexsufflation transition may be characterized by one or more parameters of the inexsufflation transition. The one or more parameters of the inexsufflation transition may include one or more of the amount of time it takes to transition from the insufflation pressure to the exsufflation pressure, the rate of change in the pressure of the pressurized flow of breathable gas from the insufflation pressure to the exsufflation pressure, and/or other parameters. In one embodiment, operation 504 is performed by a pressure generator similar to or the same as pressure generator 140 (shown in FIG. 1 and described above) under the control of a control module similar to or the same as control module 170 (shown in FIG. 1 and described above).

At an operation 506, value of a flow metric indicating the flow through the airway of the subject is determined. The value of the flow metric may be determined based on output signals generated by one or more sensors that are the same as or similar to sensor 142 (shown in FIG. 1 and described above). The value of the flow metric may be determined by a metric determination module similar to or the same as metric determination module 154.

At an operation 507, the value of the flow metric determined at operation 506 is compared with the target level of the flow metric obtained at operation 501. The comparison may include the determination of a difference between the target level of the flow metric and the determined value of the flow metric. In one embodiment, operation 507 is performed by a flow analysis module similar to or the same as flow analysis module 156 (shown in FIG. 1 and described above).

At an operation 508, an adjustment to one or more of exsufflation pressure, one or more insufflation parameters, and/or one or more parameters of the inexsufflation transition is determined. The adjustment determined based on the comparison at operation 507. The adjustment is determined to bring the flow rate in a subsequent exsufflation closer to the flow rate corresponding to the target level of the flow metric. In one embodiment, operation 508 is performed by an adjustment module similar to or the same as adjustment module 160 (shown in FIG. 1 and described above).

After operation 508, method 500 returns to operation 502, and the adjusted exsufflation pressure, one or more insufflation parameters, and/or one or more parameters of the inexsufflation transition are implement in subsequent operations.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination, Details included herein are for the purpose of illustration based on what is currently considered to be the most practical and preferred embodiments, it is to be understood that such detail is solely for that purpose and that the scope of this specification is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A method for controlling machine-induced expiratory airflow of a subject, the subject having an airway, the method comprising:
    generating a pressurized flow of breathable gas for delivery to the airway of a subject at an insufflation pressure level prior to a transition time;
    identifying the transition time based on one or more insufflation parameters;
    responsive to identification of the transition time, reducing pressure of the pressurized flow of breathable gas from the insufflation pressure level to an exsufflation pressure level;
    determining a value of a flow metric during expiration by the subject, wherein the flow metric indicates flow out of the lungs of the subject during exsufflation;
    obtaining a target level of the flow metric;
    comparing the determined value of the flow metric with the target level of the flow metric that corresponds to a target flow rate of gas out of the lungs of the subject;
    adjusting one or more of the exsufflation pressure, one or more insufflation parameters, or one or more parameters of the inexsufflation transition based on the comparison of the determined value of the flow metric with the target level of the flow metric; and
    implementing the adjusted exsufflation pressure, the adjusted one or more insufflation parameters, the adjusted one or more parameters of the inexsufflation transition, or any combination thereof during a subsequent breath.

2. The method of claim 1, wherein responsive to the determined value of the flow metric being less than the target level of the flow metric, the exsufflation pressure, the one or more insufflation parameters, the one or more parameters of the inexsufflation transition, or any combination thereof are adjusted to increase exsufflation flow during the subsequent breath.

3. The method of claim 1, wherein the flow metric comprises a flow-based metric, a volume-based metric, or a pressure-based metric.

4. The method of claim 1, wherein one or more insufflation parameters are adjusted, and the adjusted one or more insufflation parameters comprise one or more of an insufflation pressure level, an insufflation volume, an insufflation flow, or an insufflation time period.

5. The method of claim 1, wherein one or more parameters of the inexsufflation transition that are adjusted, and the adjusted one or more parameters of the inexsufflation transition comprise one or both of the amount of time it takes to transition from the insufflation pressure level to the exsufflation pressure level and the rate of change in the pressure of the pressurized flow of breathable gas from the insufflation pressure level to the exsufflation pressure level.

6. A system for controlling machine-induced expiratory airflow of a subject, the subject having an airway, the system comprising:
    a pressure generator configured to generate a pressurized flow of breathable gas for delivery to the airway of the subject; and
    one or more processors configured to execute computer program modules, the computer program modules comprising:
        a control module configured to control the pressure generator such that the pressure of the pressurized flow of breathable gas at the airway of the subject prior to a transition time is at an insufflation pressure level, and such that subsequent to the transition time the pressure level of the pressurized flow of breathable gas at the airway of the subject is at an exsufflation pressure level that is lower than the insufflation pressure level, the control module being configured to identify the transition time based on one or more insufflation parameters;
        a metric determination module configured to determine a value of a flow metric during expiration by the subject, wherein the flow metric indicates flow out of the lungs of the subject during exsufflation;
        a target module configured to obtain a target level of the flow metric;

a flow analysis module configured to compare the determined value of the flow metric with the target level of the flow metric; and an adjustment module configured to adjust one or more of exsufflation pressure, one or more of the insufflation parameters, or one or more parameters of the inexsufflation transition based on comparison by the flow analysis module.

7. The system of claim 6, wherein the adjustment module is configured such that responsive to the determined value of the flow metric being less than the target level of the flow metric, the exsufflation pressure, the one or more insufflation parameters, and/or the one or more parameters of the inexsufflation transition are adjusted to increase exsufflation flow during a subsequent breath.

8. The system of claim 6, wherein the flow metric comprises a flow-based metric, a volume-based metric, or a pressure-based metric.

9. The system of claim 6, wherein the adjustment module is configured such that one or more insufflation parameters are adjusted, and the adjusted one or more insufflation parameters comprise one or more of an insufflation pressure level, an insufflation volume, an insufflation flow, or an insufflation time period.

10. The system of claim 6, wherein the adjustment module is configured such that one or more parameters of the inexsufflation transition are adjusted, and the adjusted one or more parameters of the inexsufflation transition comprise one or both of the amount of time it takes to transition from the insufflation pressure level to the exsufflation pressure level, and the rate of change in the pressure of the pressurized flow of breathable gas from the insufflation pressure level to the exsufflation pressure level.

11. A system configured to control machine-induced expiratory airflow of a subject, the subject having an airway, the system comprising:

means for generating a pressurized flow of breathable gas for delivery to the airway of a subject at an insufflation pressure level prior to a transition time;

means for identifying the transition time based on one or more insufflation parameters;

means for, responsive to identification of the transition time, reducing pressure of the pressurized flow of breathable gas from the insufflation pressure level to an exsufflation pressure level subsequent to the transition time to initiate expiration by the subject;

means for determining value of a flow metric during expiration by the subject, wherein the flow metric indicates gas flow out of the lungs of the subject during exsufflation;

means for obtaining a target level of the flow metric;

means for comparing the determined value of the flow metric with the target level of the flow metric;

means for adjusting one or more of exsufflation pressure, one or more insufflation parameters, or one or more parameters of the inexsufflation transition based on the comparison of the determined value of the flow metric with the target level of the flow metric; and means for implementing the adjusted exsufflation pressure, the adjusted one or more insufflation parameters, the adjusted one or more parameters of the inexsufflation transition or any combination thereof during a subsequent breath.

12. The system of claim 11, wherein responsive to the determined value of the flow metric being less than the target level of the flow metric, the exsufflation pressure, the one or more insufflation parameter, the one or more parameters of the inexsufflation transition or any combination thereof are adjusted to increase exsufflation flow during the subsequent breath.

13. The system of claim 11, wherein the flow metric comprises a flow-based metric, a volume-based metric, or a pressure-based metric.

14. The system of claim 11, wherein the means for adjusting is configured such that one or more insufflation parameters are adjusted, and such that the adjusted one or more insufflation parameters comprise one or more of an insufflation pressure level, an insufflation volume, an insufflation flow, or an insufflation time period.

15. The system of claim 11, wherein the means for adjusting is configured such that one or more parameters of the inexsufflation transition are adjusted, and such that the adjusted one or more parameters of the inexsufflation transition comprise one or both of the amount of time it takes to transition from the insufflation pressure level to the exsufflation pressure level and the rate of change in the pressure of the pressurized flow of breathable gas from the insufflation pressure level to the exsufflation pressure level.

* * * * *